United States Patent [19]

Cain, deceased et al.

[11] 4,366,318

[45] Dec. 28, 1982

[54] COMPOUND HAVING ANTITUMOR PROPERTIES

[75] Inventors: Bruce F. Cain, deceased, late of Auckland, New Zealand, by Patricia J. Cain, executor; Graham J. Atwell, Auckland, New Zealand

[73] Assignee: Development Finance Corporation of New Zealand, Wellington, New Zealand

[21] Appl. No.: 257,857

[22] Filed: Apr. 27, 1981

[30] Foreign Application Priority Data

Apr. 28, 1980 [NZ] New Zealand .................. 193551

[51] Int. Cl.³ .................. C07D 219/10; A61K 31/47
[52] U.S. Cl. .................................. 546/106; 424/257
[58] Field of Search .................. 546/106; 424/257

[56] References Cited

U.S. PATENT DOCUMENTS 4,258,191 3/1981 Dubicki et al. .................. 546/106

FOREIGN PATENT DOCUMENTS 25705 3/1981 European Pat. Off. ............ 424/257

OTHER PUBLICATIONS

Cain, et al., J. Med. Chem. 20, (8), pp. 987–996 (1977).
Ferguson, et al., J. Med. Chem., 22, (3), 251–255 (1979).
Denny, et al., J. Med. Chem., 22, (12), pp. 1453–1460 (1979).
Cain, et al., J. Med. Chem., 19, (12), pp. 1409–1416 (1976).

*Primary Examiner*—Donald G. Daus
*Assistant Examiner*—Diana G. Rivers
*Attorney, Agent, or Firm*—Brumbaugh, Graves, Donohue & Raymond

[57] ABSTRACT

The compound 4'-(9-[4-[N-methyl-carboxamido]-5-methyl]acridinylamino)methanesulphon-m-anisidide and acid addition salts thereof have antitumor properties.

2 Claims, No Drawings

COMPOUND HAVING ANTITUMOR PROPERTIES

BACKGROUND OF THE INVENTION

A number of acridinylaminomethanesulfonanilide derivatives have recently been studied for antitumour activity. AMSA or 4'-(9-acridinylamino) methanesulfonanilide was found to show high antitumour activity in L1210 leukaemia screening systems (see G. J. Atwell, B. F. Cain and R. N. Seelye, *J. Med. Chem.*, 15, 611–615 (1972)). Of the derivatives of AMSA which have been studied, m-AMSA or 4'-(9-acridinylamino)-methanesulfon-m-anisidide has been shown to be highly effective in treating L1210 leukaemia and has shown promise in a number of other experimental tumour systems (see the following articles: B. F. Cain and G. J. Atwell, *Europ. J. Cancer*, 10, 539–549 (1974); B. F. Cain, G. J. Atwell and W. A. Denny, *J. Med. Chem.*, 18, 1110–1117 (1975); B. F. Cain, W. R. Wilson and B. C. Baguley, *Molecular Pharmacology*, 12, 1027–1035 (1976); B. F. Cain, G. J. Atwell and W. A. Denny, *J. Med. Chem.*, 19, 772–777 (1976); B. F. Cain and G. J. Atwell, *J. Med. Chem.*, 19, 1409–1416 (1976); M. J. Waring *Europ. J. Cancer*, 12, 995–1001 (1976); B. C. Baguley, W. R. Wilson, L. R. Ferguson and B. F. Cain, *Current Chemotherapy*, pp. 1210–1212 (1978); W. A. Denny, G. J. Atwell and B. F. Cain, *J. Med. Chem.*, 21, 5–10 (1978)).

m-AMSA has been selected for clinical trials and has generated clinical interest during Phase I and Phase II clinical studies (see D. D. Von Hoff and others, *Cancer Treatment Reports*, 62, No. 10, 1421–1426 (1978); S. S. Legha and others, *Cancer Research*, 38, 3712–3716 (1978) and B. F. Cain, U.S. patent application Ser. No. 151,927 and the literature articles numbered 22 to 58 referred to therein).

AMSA and m-AMSA have the structural formulae

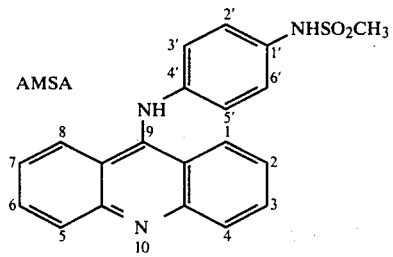

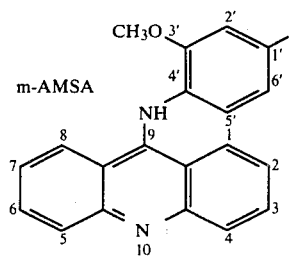

The antitumour activity of a large range of AMSA and m-AMSA analogs containing variously substituted acridine nuclei has now been investigated, see for example G. J. Atwell, B. F. Cain and R. N. Seelye, *J. Med. Chem.*, 15, 611–615 (1972); B. F. Cain, R. N. Seelye and G. J. Atwell, *J. Med. Chem.*, 17, 922–930 (1974); B. F. Cain, G. J. Atwell and W. A. Denny, *J. Med. Chem.*, 18, 1110–1117 (1975), and *J. Med. Chem.*, 19, 772–777 (1976); B. F. Cain and G. J. Atwell, *J. Med. Chem.*, 19, 1124–1129 and 1409–1416 (1976); G. J. Atwell, B. F. Cain and W. A. Denny, *J. Med. Chem.*, 20, 520–526, 987–996, 1128–1134, and 1242–1246 (1977); W. A. Denny, G. J. Atwell and B. F. Cain, *J. Med. Chem.*, 21, 5–10 (1978); W. A. Denny and B. F. Cain, *J. Med. Chem.*, 21, 430–437 (1978); B. F. Cain, B. C. Baguley and W. A. Denny, *J. Med. Chem.*, 21, 658–668 (1978); L. R. Ferguson and W. A. Denny, *J. Med. Chem.*, 22, 251–255 (1979) and W. A. Denny, G. J. Atwell and B. F. Cain *J. Med. Chem.*, 22, 1453–1460 (1979).

As clinical cancer chemotherapy improves, and patients live symptom free for longer intervals, it is obviously important that the agents employed are not themselves carcinogenic and capable of disease re-induction. Employing mutagenicity in the Ames bacterial tester strains (B. N. Ames, J. McCann, and E. Yamasaki, *Mutat. Res*, 31, 347 (1975)) as likely predictors of carcinogenicity, it was apparent to the present inventors that mutagenic activity and antitumour effectiveness did not parallel one another. Such observations suggested that the undesirable side effect of mutagenicity might therefore be eliminated.

A new class of m-AMSA analogs containing a carboxamide substituent in the 3 and/or 5 positions in the acridine nucleus which have antitumour activity in animals and low or no direct mutagenicity, as described in our U.S. patent application Ser. No. 187,517. Included within that class of analogs is the compound

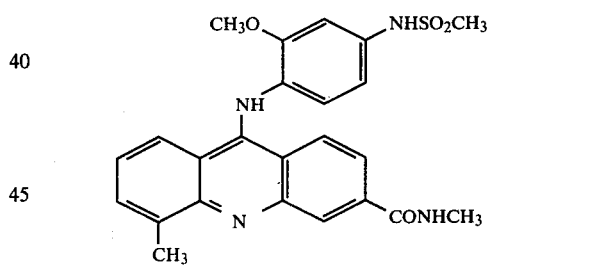

(Compound 9 of Table 1 and Example B in Specification No. 187,517).

SUMMARY OF THE INVENTION

An isomeric compound of formula (II) below has been prepared which unexpectedly has high experimental antitumour activity and is more dose potent than the parent compound m-AMSA.

It is the object of the present invention to describe this compound, a process for the preparation of the compound, and the use of the compound as an antitumour agent.

DESCRIPTION OF THE INVENTION

The novel compound of the present invention is represented by the formula

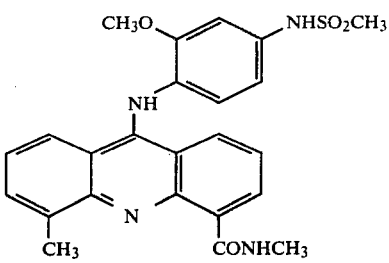

and can be named 4'-(9-[4-[N-methylcarboxamido]-5-methyl]-acridinylamino) methanesulphon-m-anisidide.

This compound of formula (II) forms acid addition salts, and these form part of the present invention. As examples of acid addition salts, there may be mentioned the pharmaceutically acceptable acid additions salts formed with hydrochloric, hydrobromic, lactic, methanesulphonic, D-gluconic, and 2-hydroxyethanesulphonic (i.e. isethionic) acids.

The compound of formula (II), and acid addition salts thereof, may be prepared by a process which comprises coupling the 9-chloroacridine of the formula

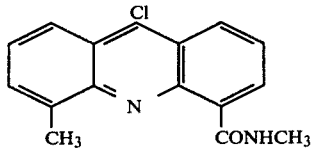

with 3-methoxy-4-aminomethanesulphonanilide of the formula

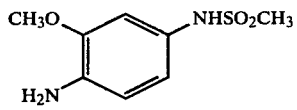

in an acid medium, and if desired, converting the compound of formula (II) into an acid addition salt thereof.

The 9-chloroacridine of formula (III) may be prepared, and the coupling of the 9-chloroacridine with the 3-methoxy-4-aminomethanesulphonanilide may be performed, according to the procedures described in Patent Specification No. 187517.

The following Example A illustrates the preparation of the compound of formula (II) and acid addition salts thereof.

EXAMPLE A

3-Methyl-N-(2-carboxyphenyl)anthranilic acid

The potassium salt of 3-methylanthranilic acid was generated by hydrogenation (Palladium-charcoal catalyst) of a solution of the potassium salt of 2-nitro-3-methylbenzoic acid (37.4 gm) in methanol-$H_2O$ (1:4 v/v) with following clarification and evaporation to dryness. To this potassium salt were added 2-chlorobenzoic acid (34.5 gm), $K_2CO_3$ (34.5 gm), catalytic Cu powder (0.3 gm), CuBr (0.3 gm), N-methyl-2-pyrrolidone (45 ml) and 2-ethoxyethanol (45 ml) and the mixture was heated in an oil bath at 150° C. with stirring for 2½ hr. Water (1.5 L) was added to the cooled mixture and the whole warmed until the salts had dissolved and crude product was precipitated from the clarified solution by acidiciation with excess HOAc. The product was washed well with boiling water, then dissolved in 5% aqueous $Na_2CO_3$ (500 ml) and decolourising charcoal (5 gm) stirred in. To the boiling clarified solution EtOH (500 ml) was added and the mixture acidified by the slow addition of HOAc. The crystalline diacid which separated from the hot solution was collected, washed with boiling water and dried (48.9 gm). Crystallisation from EtOH—$H_2O$ provided homogeneous material as colourless needles of mp 258°-259° C.

4-Methyl-9(10H)acridone-5-carboxylic acid

The preceeding product (44.5 gm) was stirred with $H_2SO_4$ (d 1.84; 120 ml) at 90° C. for 4.5 hr. The cooled mixture was stirred into $H_2O$ (1.5 L) and the precipitated product collected and washed well with $H_2O$. The dried product was dissolved in a mixture of N, N-dimethylformamide (DMF; 200 ml), EtOH (300 ml) and $H_2O$ (500 ml) containing 12 N $NH_3$ (30 ml) by warming and stirring. The clarified solution was heated to boiling and acidified with HOAc. After cooling, the pure acridone was collected as bright yellow prismatic crystals of mp 357° C. (dec.).

The Compound of Formula (II)

4-Methyl-9(10H)acridone-5-carboxylic acid (16.0 gm) was suspended in $SOCl_2$ (85 ml) containing DMF (0.1 ml) and the suspension was heated under reflux conditions until a solution resulted and then for a further ½ hr. Excess $SOCl_2$ was removed in vacuo and final traces were removed by addition of a little anhydrous dioxan and reevaporation. The resulting solid was suspended in an ice-cooled mixture of EtOH-free $CHCl_3$ (300 ml) and 24% w/v aqueous $CH_3NH_2$ (40 ml) and the mixture stirred vigorously at 0° C. until all solids had dissolved. After addition of $H_2O$ (100 ml) the $CHCl_3$ layer was separated, washed with $H_2O$ (2×200 ml) dried ($Na_2SO_4$) and filtered. A solution of 3'-methoxy-4'-aminomethane-sulphonanilide (14.5 gm) in MeOH (200 ml) was then added followed by 12 N HCl (0.2 ml). The mixture was boiled for ½ hr. while stirring and the solvent distilled until the volume was reduced to 250 ml, when boiling EtOAc (200 ml) was added. Following thorough cooling, the product hydrochloride salt was collected and washed with EtOAc. This salt (29.2 gm) was suspended in DMF and $H_2O$ (1:3; v/v) (100 ml) $KHCO_3$ (7.0 gm) added and the mixture stirred at 50° for 6 hr. then thoroughly cooled and the free base of compound (II) collected and washed thoroughly with $H_2O$. The dried base (26.1 gm) was suspended in DMF (60 ml) at room temperature and a solution of isethionic acid (7.45 gm) in MeOH (50 ml) added and the mixture stirred until a solution resulted. Following clarification, the isethionate salt of compound (II) was precipitated by addition of excess EtOAc-light petroleum (1:1; v/v). The resulting salt (31.9 gm) was dissolved in boiling MeOH (950 ml), clarified, hot EtOAc (800 ml) was added and the solution distilled until crystallisation initiated. Following thorough cooling, the pure isethionate salt was collected and washed well with EtOAc and dried. Pure product compound (II) isethionate salt (29.6 gm) was obtained as orange-red crystals of mp 254°-256° C.

The compound (II) unexpectedly has high experimental antitumour activity and is more dose potent than m-AMSA. Compound (II) has the marked advantage that it is well absorbed orally, in distinction to m-AMSA and most other analogs of m-AMSA. The compound (II) is therefore indicated for use as an antitumour or anticancer agent and may be formulated in pharmaceutical forms conventional for the administration of such agents to patients.

Accordingly, the present invention also provides pharmaceutical compositions having antitumour activity and comprising the compound of formula (II), or a pharmaceutically acceptable acid addition salt thereof, and one or more pharmaceutically acceptable carriers or diluents.

In a further aspect, the present invention provides a method for treating tumours and in particular cancers in a patient which comprises administering to the patient an antitumour effective amount of the compound of formula (II), or a pharmaceutically acceptable acid addition salt thereof.

The following Example B illustrates the animal tumour testing showing the marked superiority of compound (II), as the isethionate salt, compared to m-AMSA isethionate, when the compounds are administered by the oral route.

EXAMPLE B

Lymphocytic Leukemia P388 Test

The animals used are DBA2 mice all of one sex and weighing between 18.5 and 21.5 grams. The tumour transplant is by subcutaneous inoculation above the right axilla of 0.1 ml of dilute ascitic fluid containing $10^6$ cells of lymphocytic leukemia P388. The test compounds have been administered orally (p.o.) or intravenously (i.v.) on days 1, 5 and 9, relative to tumour implantation, at various doses. With oral dosing animals have been starved for twelve hours immediately preceding drug administration. There are 10 animals per test group and 30 in any control group. The animals are weighed and survivors are recorded on a regular basis for 60 days. The mean survival time and the ratio of survival time for treated (T)/control (C) animals are calculated. The criterion for efficacy is T/C% > 120.

breast cancer, cellular hepatoma, melanoma, etc. The preferred route of administration is intravenous and the dose generally employed is from about 20 mg to about 500 mg/m$^2$ of body surface per day for one to five days preferably 30 mg to 100 mg/m$^2$ per day for about three days. The procedure may be repeated about every three weeks.

The compounds of the present invention may also be administered orally in the form of capsules, tablets, syrups, etc., or rectally in the form of suppositories. Generally, higher doses ae employed when using these routes, especially orally. Thus, when employing these routes about 20 mg to about 1.0 g/m$^2$ of body surface per day for from one to five days, preferably 50 mg to 800 mg/m$^2$ per day for about three days is used.

The compounds of the invention, when administered intravenously, are generally dissolved in water, sterifiltered, lyophilized and redissolved at the time of use. Preferably, an excess of acid is present to further improve solubility and minimize the chances of any blockage of the pores during the sterifiltration step. An excess of an acid is less desirable if the sterilization process does not utilize a microfiltration step. The lyophilized material is dissolved in a non-toxic aqueous vehicle prior to administration. The vehicle may contain buffers, materials, to make the resultant solution isotonic, preservatives, etc., which are compatable with the compounds of this invention. Certain ions, such as halide ion, cause precipitation of the hydro halide salt of compound (II) and should be avoided.

In addition, the compounds of the present invention are orally administered, for example, with an inert diluent or with an assimilable edible carrier, or they may be compressed into tablets, or they may be incorporated directly with the food of the diet. For oral therapeutic administration, the compounds of this invention may be incorporated with excipients and used in the form of tablets, troches, capsules, elixirs, suspensions, syrups and the like. Such compositions and preparations should

| Compound | Administration route | Dose (mg./kg.) | Mean Survival (Days) | T/C % |
|---|---|---|---|---|
| 4'-(9-[4-[N—Methylcarboxamido]-5-methyl]acridinylamino)methane-sulphon-m-anisidide isethionate | p.o. | 75 | 11.2 | 74 |
| | | 50 | 22.6 | 150 |
| | | 33 | 22.3 | 148 |
| | | 22 | 19.3 | 128 |
| | | 14.7 | 16.8 | 111 |
| | Control | 0 | 15.1 | |
| | i.v. | 45 | 9.7 | 62 |
| | | 30 | 24.2 | 153 |
| | | 20 | 24.0 | 152 |
| | | 13.3 | 20.7 | 131 |
| | | 9 | 19.4 | 123 |
| | Control | 0 | 15.8 | |
| 4'-(9-Acrindinylamino)-methanesulphon-m-anisidide isethionate | p.o. | 400 | 15.6 | 103 |
| | | 267 | 14.8 | 98 |
| | | 178 | 15.2 | 101 |
| | Control | 0 | 15.1 | |
| | i.v. | 61.5 | 10.6 | 67 |
| | | 41 | 19.4 | 123 |
| | | 27 | 22.3 | 141 |
| | | 18 | 19.0 | 120 |
| | Control | 0 | 15.8 | |

The compounds of the present invention, i.e. the compound (II) and the pharmaceutically acceptable salts thereof, are useful antitumour or anti neoplastic agents in the treatment of mammals, such as dogs, cats, etc. Typical of the disease states wherein the compounds of this invention may be employed are leukemia, contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavouring agent such as peppermint.

The compounds of this invention may be administered in combination with other antineoplastic agents. The anti-neoplastics may be derived from the numerous classes of agents; such as: antibiotic derivatives, doxorubicin, mitomycin, actinomycin, etc.; antiestrogen agents, such as tamoxifen; antimetabolites, such as fluorouracil, carmustine, lomustine, methotrexate, mercaptopurine, thioguanine, etc.; cytotoxic agents, such as bleomycin, cyclophosphamide, bisulfan, procarbazine, hyroxyurea, etc.; hormones such as dromostanolone, ethinyl estradiol, megestrol, prednisone, methyltestosterone, chlorotrianisene, testolactone, etc.; nitrogen mustard derivatives, such as melphalan, chlorambucil, methlorethamine, TESPA, etc.; steroids, such as betamethasone, prednisolone, etc., and other miscellaneous agents, such as vinblastine, vincristine, asparaginase, mitotane, cisplatin, etc. When using combinations of two or more antineoplastic agents, the dosage of compound (II) or salt thereof may be reduced. The dosage ranges generally employed for the above cited antineoplastics which may be used with compound (II) are known to the medical profession, see Physicians' Desk Reference, 34th Edition, Medical Economics Co. 1980, which is incorporated by reference.

The following Examples illustrate pharmaceutical compositions comprising compound (II), referred to in these examples as "anisidide".

EXAMPLE C

Anisidide Gluconate Lyophilized Injectable Formulation

|  | per liter |
|---|---|
| 1. Anisidide Gluconate (11.77 mg/ml*) | 11.77 g |
| 2. Gluconic Acid, 50% Solution | q.s. |
| 3. Celite 521** | 1.5 g |
| 4. Water for Injection, USP q.s. to make | 1000 ml |

*Equivalent to 7.5 mg/ml of anisidide plus 3% intentional excess.
**If needed to clarify solution.

Method of Preparation (for 1000 ml)

A. Add sufficient 2 to approximately 900 ml of 4 in a suitable container to adjust the pH of the solution to approximately 2.2.

B. Add 1 slowly with continuous stirring until 1 completely dissolves.

C. Recheck pH and adjust to 2.3-2.7, if needed, with 2.

D. Add a sufficient amount of 4 to make 1000 ml of solution and mix well

E. If necessary, clarify solution with 3 followed by suitable filtration to remove 3 (Whatman No. 1 filter paper, Millipore AW 19 membrane or equivalent).

F. Sterilize solution by filtration through a previously sterilized membrane (Millipore GS or equivalent) using appropriate prefiltration, if necessary.

G. Aseptically fill into previously sterilized vials (10 ml per vial).

H. Stopper vials loosely with rubber lyophilization stoppers and lyophilize in a suitable lyophilizer, (75 mg anisidide per vial).

I. At the conclusion of the lyophilization cycle, stopper and cap vials.

EXAMPLE D

Anisidide Gluconate Injectable Formulation

|  | per 1000 vials |
|---|---|
| Anisidide gluconate (117.7 mg/vial*) | 117.7 g |

*Equivalent to 75 mg of anisidide + 3% intentional excess.

Method of Preparation

1. Presterilize the anisidide gluconate.
2. Fill into appropriate ** (10 ml-20 ml) previously sterilized vials.
3. Stopper and cap vials.

**If 10 ml vials are used and 10.0 ml of Sterile Water for injection is used to dissolve the sterile powder, the resulting concentration will be equivalent to 7.5 mg/ml, anisidide, as the gluconate. If 20 ml vials are used and 20.0 ml of Sterile Water for Injection is used to dissolve the sterile powder, the resulting concentration will be 3.75 mg/ml.

EXAMPLE E

Anisidide Gluconate Oral Formulation

|  | mg/cap | g/1000 caps |
|---|---|---|
| 1. Anisidide Gluconate | 76.1* mg | 76.2 g |
| 2. Lactose USP Hydrous | 438.8 | 438.8 |
| 3. Polysorbate 80 USP | 5.0 | 5.0 |
| 4. Syloid 74 (silica gel) | 10.0 | 10.0 |
| 5. Alcohol SD 3A Anhydrous | 0.07 ml | 7.0 ml |
|  | 530 mg | 530 g |

*Equivalent to 50 mg anisidide Base.

Method of Preparation

A. Dissolve 3 in 5 and add to 4 conatined in a suitable blender. Blend thoroughly. Transfer the wet mass onto trays and dry at about 120° F. overnight. Add to 2 and mix well.

B. Screen 1 through a No. 60 screen. Add material from Step A and blend thoroughly. Pass through No. 60 screen and reblend.

C. Fill 530 mg of the powder mixture into No. "O" dark brown opaque hard gelatin capsules.

What is claimed is:

1. The compound 4'-(9-[4-[N-methyl-carboxamido]-5-methyl]acridinylamino)methanesulphon-m-anisidide, represented by the formula

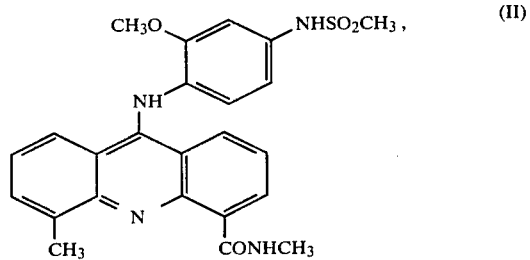

or an acid addition salt thereof.

2. The isethionate salt of 4'-(9-[4-[N-methyl-carboxamido]-5-methyl]acridinylamino)methanesulphon-m-anisidide.

* * * * *